United States Patent [19]

Vesely et al.

[11] Patent Number: 5,779,638
[45] Date of Patent: Jul. 14, 1998

[54] ULTRASOUND-BASED 3-D TRACKING SYSTEM USING A DIGITAL SIGNAL PROCESSOR

[75] Inventors: Ivan Vesely, Cleveland Heights, Ohio; Wayne L. Smith, London, Canada

[73] Assignee: Sonometrics Corporation, London, Canada

[21] Appl. No.: 842,807

[22] Filed: Apr. 17, 1997

Related U.S. Application Data

[63] Continuation-in-part of Ser. No. 411,959, PCT/CA96/00194 filed on Mar. 24, 1996 now PCT/WO96/31753, Pat. No. 5,515,853.

[51] Int. Cl.$^6$ .................................................. A61B 8/00
[52] U.S. Cl. .................................................. 600/437
[58] Field of Search .......................... 600/437, 447, 600/448, 509, 515, 897, 898, 916; 364/724.1, 724.12, 724.14, 728.04, 728.05; 342/21, 27; 375/200, 256

[56] References Cited

U.S. PATENT DOCUMENTS

| | | | |
|---|---|---|---|
| 4,743,906 | 5/1988 | Fullerton | 342/27 |
| 5,398,183 | 3/1995 | Elliott | 600/509 |
| 5,438,531 | 8/1995 | Shank | 364/724.1 |

*Primary Examiner*—George Manuel
*Attorney, Agent, or Firm*—Benesch, Friedlander, Coplan & Aronoff LLP

[57] ABSTRACT

A system for determining a time delay of a signal propagating through a medium. The time delay is used to determine the distance between transducers arrangable within a body. One or more Digital Signal Processors (DSP) are programmed to recognize various waveform patterns by matching a received waveform to a template waveform.

18 Claims, 4 Drawing Sheets

5,779,638

ULTRASOUND-BASED 3-D TRACKING SYSTEM USING A DIGITAL SIGNAL PROCESSOR

This is a continuation-in-part of International Application Serial No. PCT/CA96/00194, filed on Mar. 24, 1996 and now PCT/WO96/31753, which is a CIP of 08/411,959 filed Mar. 28, 1995, now U.S. Pat. No. 5,515,853.

FIELD OF INVENTION

The present invention relates generally to an ultrasound based 3-D tracking system, and more particularly to an ultrasound based 3-D tracking system using a digital signal processor to determine travel time for ultrasonic sound waves to isolate relative positions of objects.

BACKGROUND OF THE INVENTION

Using the time-of-flight principle of high frequency sound waves, it is possible to accurately measure distances within an aqueous medium, such as inside the body of a living being during a surgical procedure. High frequency sound, or ultrasound, is defined as vibrational energy that ranges in frequency from 100 kHz to 10 MHz. The device used to obtain three-dimensional measurements using sound waves is known as a sonomicrometer. Typically, a sonomicrometer consists of a pair of piezoelectric transducers (i.e., one transducer acts as a transmitter while the other transducer acts as a receiver). The transducers are implanted into a medium, and connected to electronic circuitry. To measure the distance between the transducers, the transmitter is electrically energized to produce ultrasound. The resulting sound wave then propagates through the medium until it is detected by the receiver.

The transmitter typically takes the form of a piezoelectric crystal that is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver also typically takes the form of a piezoelectric crystal (with similar characteristics to the transmitter piezoelectric crystal), that detects the sound energy produced by the transmitter and begins to vibrate in response thereto. This vibration produces an electronic signal in the order of millivolts, that can be amplified by appropriate receiver circuitry.

The propagation velocity of ultrasound in an aqueous medium is well documented. The distance traveled by a pulse of ultrasound can therefore be measured simply by recording the time delay between the instant the sound is transmitted and when it is received.

In the prior art, counters and threshold detect circuitry have been used to determine the travel time of the waveforms transmitted between the transducers. A counter is associated with each transducer and waveforms are used as a trigger for the counter. Threshold detect circuitry stops the counter when a rising voltage crosses above the noise level. Using counters and threshold detect circuitry for determining travel time limits precision to the counter frequency and requires a significant number of components.

The present invention provides a unique and advantageous system using a digital signal processor (DSP) to determine a propagation delay time for the purpose of tracking the position of a device moving through a medium.

SUMMARY OF THE INVENTION

According to the present invention there is provided a digital signal processor (DSP) for matching a received waveform to a template waveform and determining a waveform travel time.

An advantage of the present invention is the provision of a digital signal processor (DSP), which eliminates the need for counters and associated waveform triggering circuitry.

Another advantage of the present invention is the provision of a DSP which can sample and digitize analog signals at a very high rate.

Another advantage of the present invention is the provision of a DSP programmed to recognize various waveform patterns.

Still other advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

Figure 1:
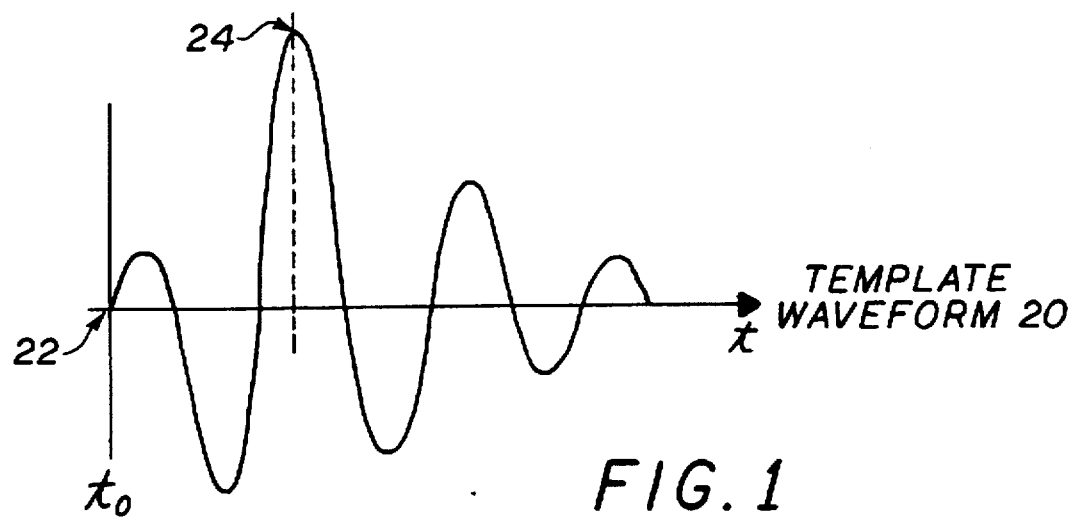
FIG. 1 is a diagram of a template waveform.
Figure 2:
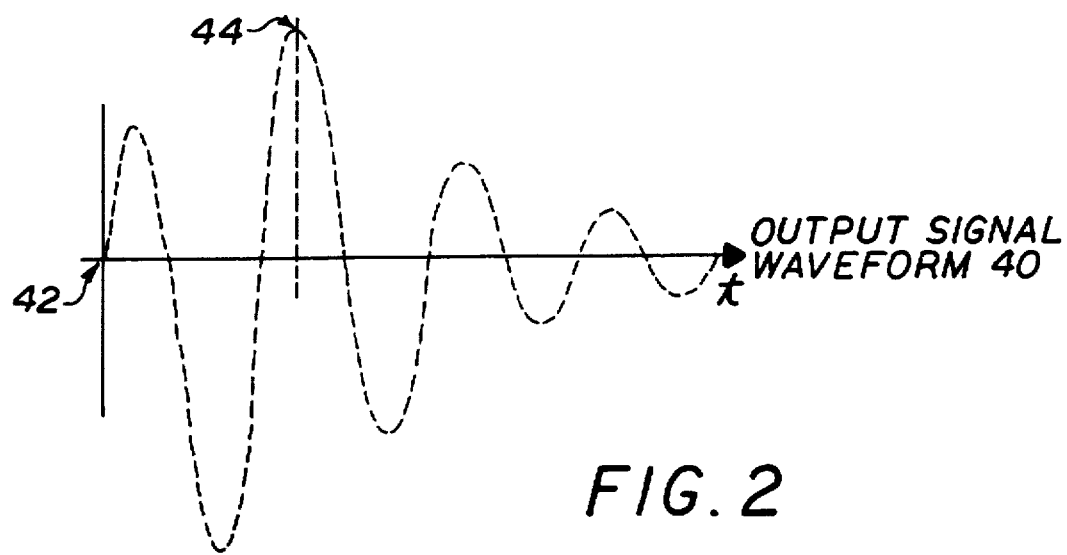
FIG. 2 is a diagram of an output signal waveform.

Referring now to the drawings wherein the showings are for the purposes of illustrating a preferred embodiment of the invention only and not for purposes of limiting same, FIG. 1 shows a template waveform 20 having a start point 22 and a peak point 24. Template waveform 20 is characteristic of a typical electronic signal generated by an piezoelectric transducer crystal when activated in response to a sound wave. As indicated above, a piezoelectric transducer will vibrate in response to receipt of a sound wave. The vibration in turn produces an electronic signal (i.e., "output signal waveform"). FIG. 2 shows a characteristic output signal waveform 40 generated by an actual piezoelectric transducer crystal, when activated by an ultrasonic sound wave. Output signal waveform 40 has a start point 42 and a peak point 44. A digital signal processor (DSP) is programmed to compare output signal waveform 40 to template waveform 20 stored in memory.

When an output signal waveform 40 is received by the DSP, it is suitably digitized at a high sampling rate. A higher sampling rate provides a more accurate digital representation of the wave, and minimizes the chance of a loss of short duration transients. Thereafter, output signal waveform 40 (in digital form) is convolved with template waveform 20.

Figure 3:
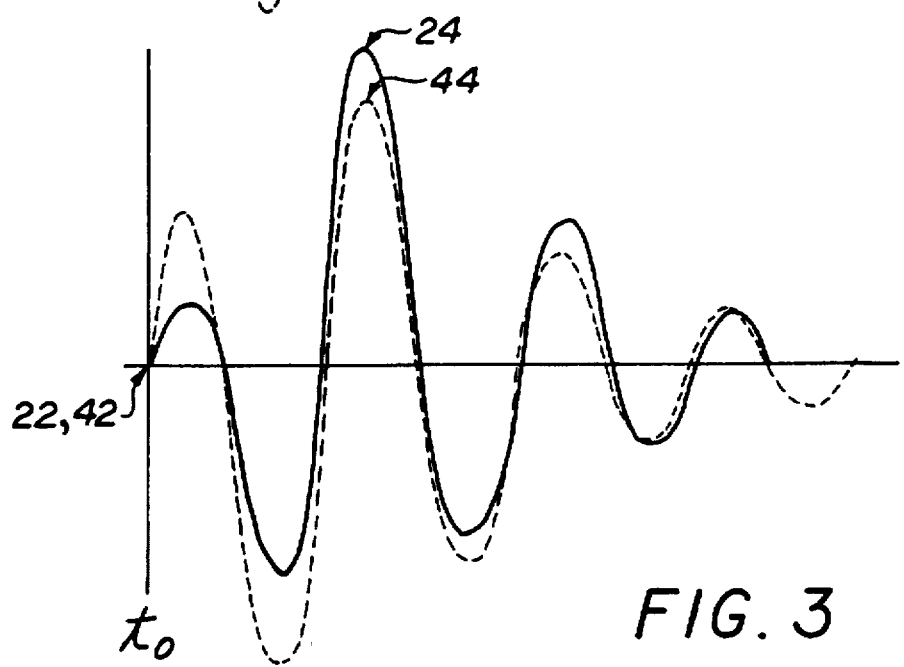
FIG. 3 is a diagram of an output signal waveform superimposed over a template waveform.

The convolution or autocorrelation process will produce a maximum at a point where these two signals have the best match, as seen in FIG. 3. It should be appreciated that an autocorrelation function provides a measure of the similarity between delayed and undelayed versions of a signal, expressed as a delay function.

By matching a point (e.g., peak point 44) on output signal waveform 40 with the corresponding point (e.g., peak point 24) on template waveform 20, start point 42 of output signal waveform 40 can be determined. In this respect, start point 42 is matched with start point 22. By matching start point 42 of output signal waveform 40 with start point 22 of template waveform 20, the time delay ($T_{delay}$) between the energizing (i.e., "firing") of a transmitter transducer and the generation of output signal waveform 40 by a receiver transducer can be determined. Accordingly, the distance between a pair of transducers can be computed.

Figure 4:
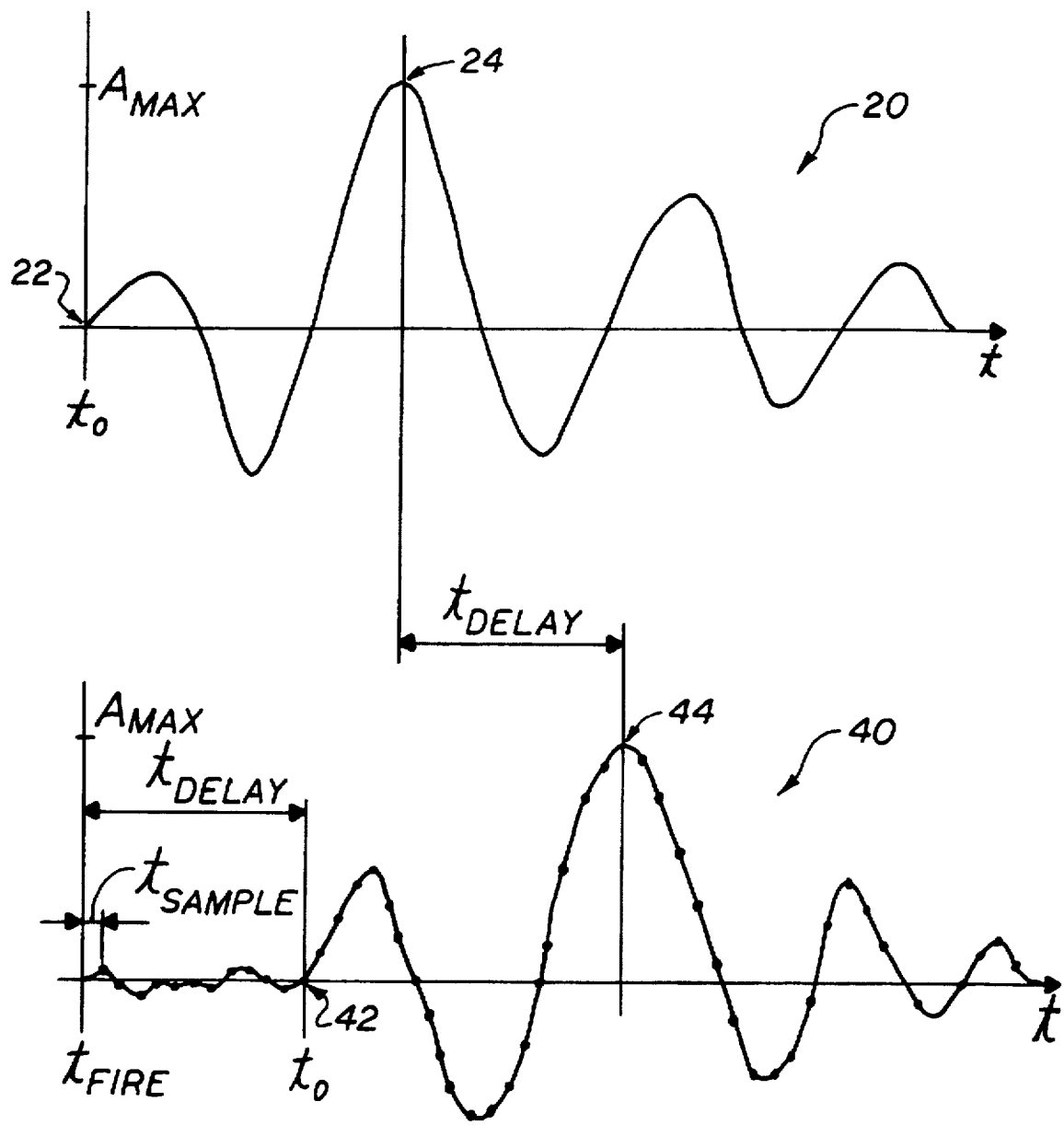
FIG. 4 is a timing diagram for a first embodiment of the present invention.

In the embodiment illustrated by the timing diagram shown in FIG. 4, the DSP begins sampling and digitizing data at the moment the transmitter transducer is "fired" ($t_{fire}$). It should be noted that "firing" refers to energization of a transducer by a voltage spike or impulse function, causing the piezoelectric crystal to oscillate at its own characteristic resonant frequency. The DSP will sample and digitize noise (from the receiver transducer) until output signal waveform 40 is received at $t_0$. Each item of digitized data is stored at an individual memory location in a memory array. Accordingly, if the incoming data is sampled at a rate of 1 MHZ, then digitized data will be stored every 1 microsecond (sampling period). Therefore, each consecutive memory location in the array represents 1 microsecond of elapsed time. It then follows that the product of: (1) the position in the memory array corresponding to $t_0$ and (2) the sampling period ($t_{sample}$), will provide a measure of the time delay ($t_{delay}$). As indicated above, the position of $t_0$ in the memory array is determined by convolving output signal waveform 40 with template waveform 20. Once the time delay ($t_{delay}$) is determined, the distance between a given pair of transducers can be computed.

As can be seen from FIG. 4, the time delay ($t_{delay}$) is represented by the distance between start point 42 and start point 22. Likewise, the time delay ($t_{delay}$) is also represented by the distance between peak position 44 and peak position 24.

It should be noted that in most cases a DSP would be required for each receiver transducer in this embodiment, unless all of the received channels are multiplexed together and passed onto one or more DSPs. The foregoing procedure replaces the need for counters (which act as timers) and threshold detect circuitry for triggering the counters.

An alternative embodiment of the present invention will now be described with reference to FIG. 5. In this embodiment, the DSP will wait for a predetermined period of time ($t_{wait}$) before beginning to sample and digitize the incoming signal. The value of $t_{wait}$ is determined such that the DSP begins sampling and digitizing the incoming signal just before the DSP is expected to receive output signal waveform 40. A counter (acting as a timer) is used to determine the value of $t_{wait}$. The counter is started at the moment the transmitter transducer is "fired." When a predetermined period of time has elapsed, the counter is stopped. The value of the counter is indicative of the value of $t_{wait}$. Just as in the case of the first embodiment described above, the DSP will sample and digitize noise until output signal waveform 40 is received. The period of time during which noise is sampled and digitized is referred to as $t_{noise}$.

Figure 5:
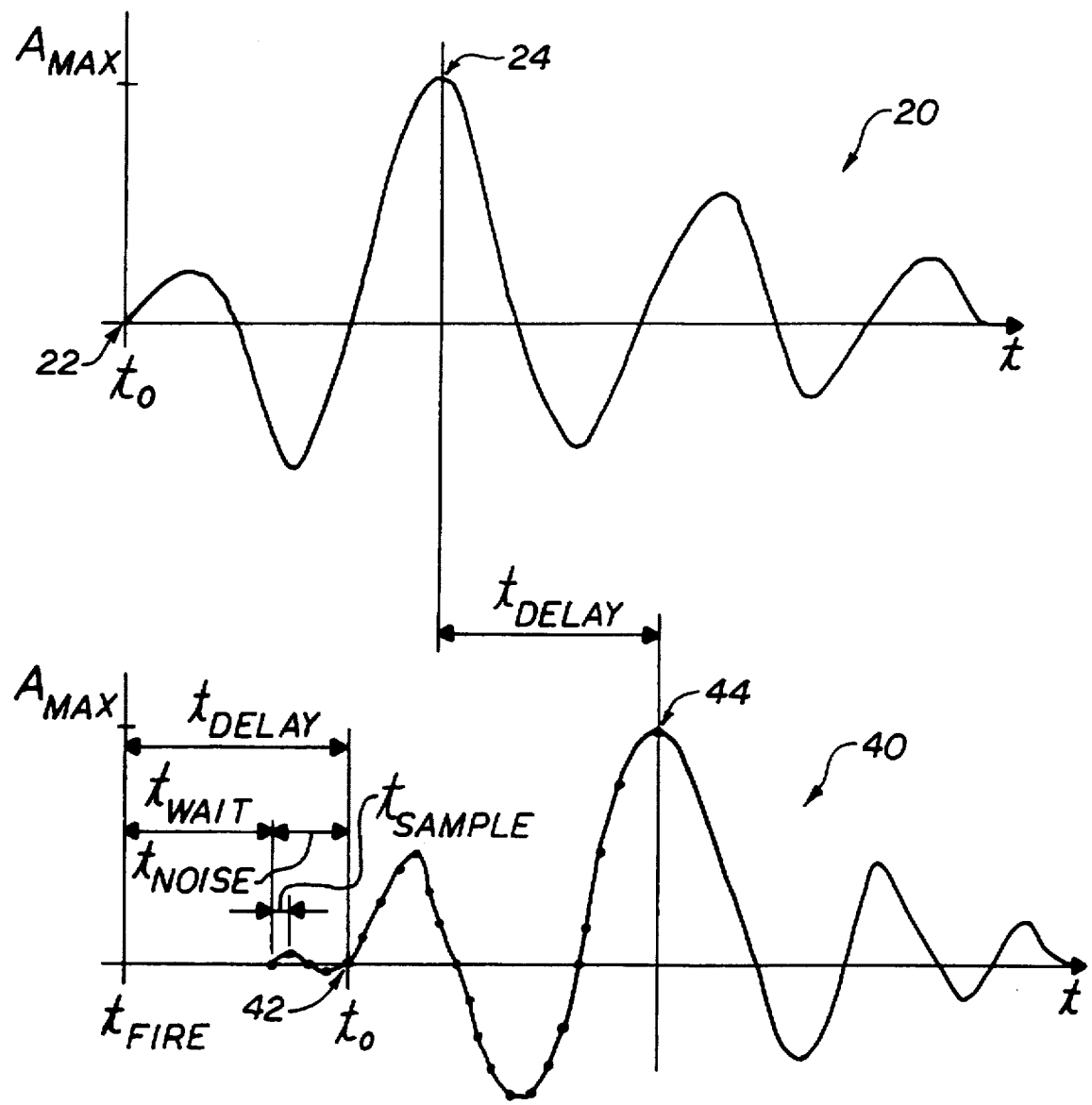
FIG. 5 is a timing diagram for a second embodiment of the present invention.

As can be seen from FIG. 5, the sum of $t_{wait}$ and $t_{noise}$ is equal to $t_{delay}$. The value of $t_{noise}$ is determined in the same manner as the value of $t_{delay}$ is determined in the first embodiment described above. The value of $t_{noise}$ is added to the value of $t_{wait}$ to compute $t_{delay}$. It should be appreciated that $t_{wait}$ can be adjusted if necessary to avoid missing any portion of output signal waveform 40, or to avoid digitizing to much noise prior to receipt of output signal waveform 40.

It should be noted that while the first embodiment eliminates the need for a threshold detect circuit (which stops a timing device when the rising voltage crosses a threshold above the noise level) and a timing device (such as a counter), it also places great demands on the DSP and requires sufficient memory to store large quantities of digitized sampling data. In contrast, the second embodiment only eliminates the need for a threshold detect circuit. However, the demand on the DSP is less, and less memory is needed since fewer data points are recorded.

Figure 6:
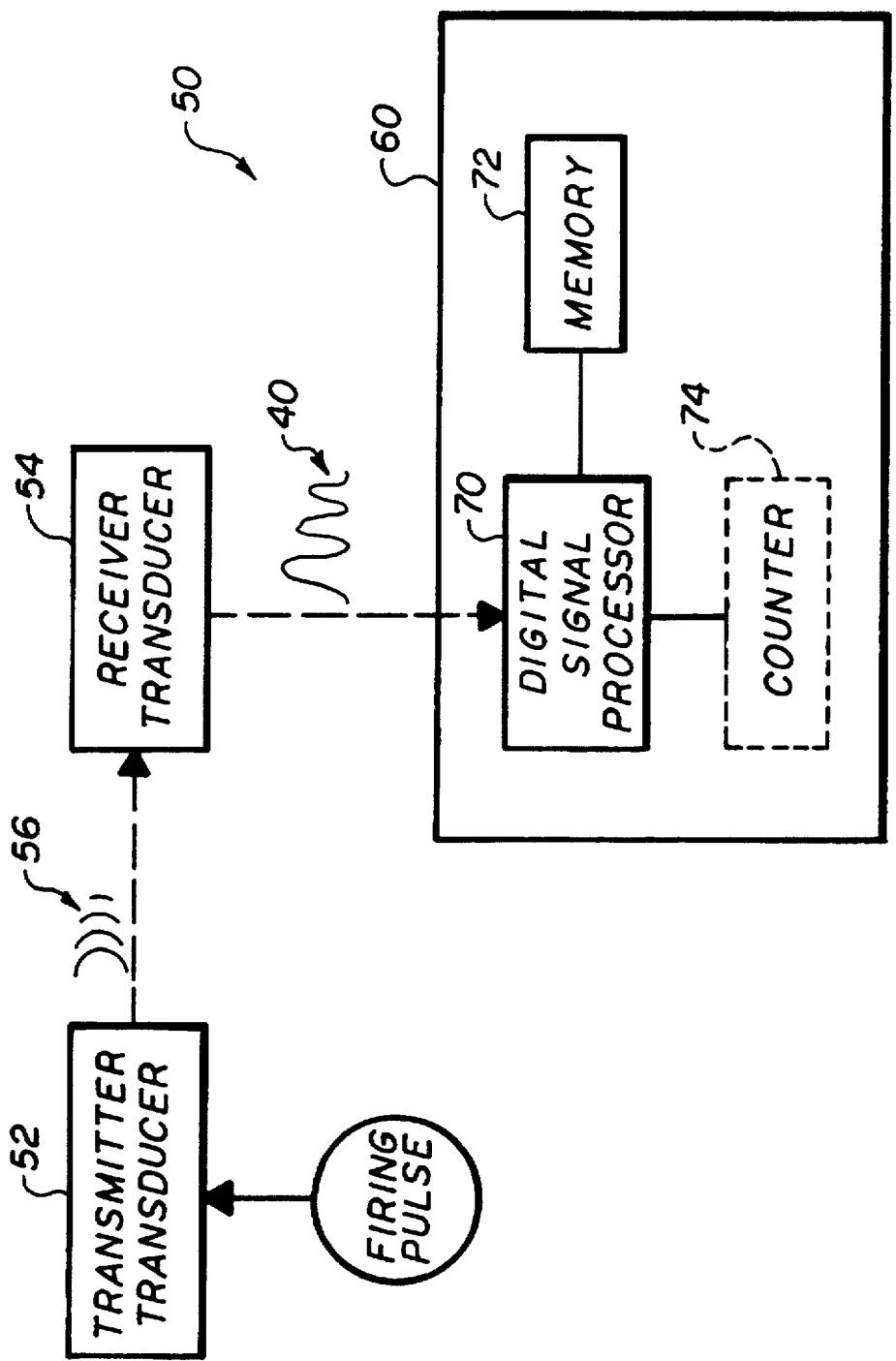
FIG. 6 is a block diagram of a system according to the present invention.

Turning now to FIG. 6, there is shown a block diagram of a system 50 according to the present invention. System 50 is generally comprised of a transmitter transducer 52, a receiver transducer 54 and a 3-D tracking system 60. 3-D tracking system 60 includes a digital signal processor (DSP) 70, a memory 72 and a counter 74(in the case of the second embodiment described above). Memory 72 stores template waveform 20, as well as the digitized samples of output signal waveform 40. It should be appreciated that 3tracking system 60 includes additional component which are described in detail in U.S. Pat. No. 5,515,853 and PCT Application No. WO96/31753.

As indicated above, transmitter transducer 52 is fired by a firing pulse. In response thereto, a sound wave 56 is generated and received by receiver transducer 54. Receiver transducer 54 responds to sound wave 56 by generating output signal waveform 40, which is received by DSP 70. DSP 70 uses the template waveform stored in memory 72 to determine a propagation time delay, and thus compute the distance between transmitter transducer 52 and receiver transducer 54.

Yet another embodiment of the subject invention suitably employs application of a suitable curve filtering algorithm to captured intervals. Reducing data to equations is suitably accomplished by any number of readily available algorithms or systems. A direct, mathematical analysis and comparison between such equations would therefore allow for matching of the waveforms.

The invention has been described with reference to a preferred embodiment. Obviously, modifications and alterations will occur to others upon a reading and understanding of this specification. It is intended that all such modifications and alterations be included insofar as they come within the scope of the appended claims or the equivalents thereof.

Having thus described the invention, it is now claimed:

1. A system for determining a propagation time delay of a transmit waveform initiated by an associated transmitter means and received by an associated receiver means, wherein said receiver means generates an output in the form of an output waveform in response to receipt of the transmit waveform, the system comprising:

template storage means for storing template waveform data representative of a characteristic output waveform;

sampling means for sampling the output of the receiver means at a predetermined sampling rate and converting the output waveform to digital output waveform data;

comparison means for comparing the digital output waveform data to the template waveform data to determine the digital output waveform data corresponding to the beginning of the output waveform; and computation means for computing the propagation time delay in accordance with the digital output waveform data corresponding to the beginning of the output waveform.

2. A system according to claim 1, wherein said comparison means includes a convolving means for convolving said digital output waveform data and said template waveform data.

3. A system according to claim 1, wherein said comparison means includes an autocorrelation means for correlating said digital output waveform data with said template waveform data.

4. A system according to claim 1, wherein said transmitter means and receiver means are piezoelectric transducer means.

5. A system according to claim 4, wherein said characteristic output waveform is characteristic of piezoelectric crystal oscillations.

6. A system according to claim 1, wherein said sampling means stores the digital output waveform data in a memory array having a respective position for each item of digital output waveform data, and said computation means includes means for computing the product of (1) the position in the memory array of the digital output waveform data corresponding to the beginning of the output waveform and (2) the predetermined sampling rate, wherein said product is indicative of the propagation time delay.

7. A system according to claim 1, wherein said system further comprises a timer means for determining a waiting time beginning with initiation of the transmit waveform and ending before generation of the output waveform.

8. A system according to claim 7, wherein said sampling means stores the digital output waveform data in a memory array having a respective position for each item of digital output waveform data, and said computation means includes means for computing the product of (1) the position in the memory array of the digital output waveform data corresponding to the beginning of the output waveform and (2) the predetermined sampling rate, and means for summing the product with said waiting time, wherein the sum is indicative of the propagation time delay.

9. A system according to claim 8, wherein said timer means includes a counter means.

10. A method for determining a propagation time delay of a transmit waveform initiated by an associated transmitter means and received by an associated transmitter means, wherein said receiver means generates an output in the form of an output waveform in response to receipt of the transmit waveform, the method comprising:

obtaining template waveform data representative of a characteristic output waveform;

sampling the output of the receiver means at a predetermined sampling rate and converting the output waveform to digital output waveform data;

comparing the digital output waveform data to the template waveform data to determine the digital output waveform data corresponding to the beginning of the output waveform; and computing the time delay in accordance with the digital output waveform data corresponding to the beginning of the output waveform.

11. A method according to claim 10, wherein said step of comparing includes the step of convolving said digital output waveform data and said template waveform data.

12. A method according to claim 10, wherein said comparing step includes the step of correlating said digital output waveform data with said template waveform data.

13. A method according to claim 10, wherein said transmitter means and receiver means are piezoelectric transducer means.

14. A method according to claim 13, wherein said characteristic output waveform is characteristic of piezoelectric crystal oscillations.

15. A method according to claim 10, wherein said step of sampling includes the step of storing the digital output waveform data in a memory array having a respective position for each item of digital output waveform data, and said step of computing includes the step of computing the product of (1) the position in the memory array of the digital output waveform data corresponding to the beginning of the output waveform and (2) the predetermined sampling rate, wherein said product is indicative of the propagation time delay.

16. A method according to claim 10, wherein said method further comprises the step of determining a waiting time beginning with initiation of the transmit waveform and ending before generation of the output waveform.

17. A method according to claim 16, wherein said step of sampling includes the step of storing the digital output waveform data in a memory array having a respective position for each item of digital output waveform data, and said step of computing includes the steps of:

(a) computing the product of (1) the position in the memory array of the digital output waveform data corresponding to the beginning of the output waveform and (2) the predetermined sampling rate, and (b) summing the product with said waiting time, wherein the sum is indicative of the propagation time delay.

18. A method for determining a time delay of a signal propagating through a medium comprising:

initiating a transmit waveform from a first location;

generating an output waveform at a second location in response to receipt of the transmit waveform;

storing template waveform data representative of a standard output waveform;

digitizing the output waveform into digital output waveform data; and comparing the digital output waveform data to the template waveform data to determine the time delay between initiation of the transmit waveform and generation of the output waveform.

\* \* \* \* \*